United States Patent
Liu et al.

(10) Patent No.: US 12,303,500 B2
(45) Date of Patent: May 20, 2025

(54) METHOD FOR IMPROVING STABILITY OF LOW-CONCENTRATION ATROPINE OPHTHALMIC PREPARATION

(71) Applicant: SHENYANG XINGQI PHARMACEUTICAL CO., LTD., Shenyang (CN)

(72) Inventors: Jidong Liu, Shenyang (CN); Kun Gao, Shenyang (CN); Jiuliang Wang, Shenyang (CN); Qiang Yang, Shenyang (CN)

(73) Assignee: SHENYANG XINGQI PHARMACEUTICAL CO., LTD., Shenyang (CN)

( * ) Notice: Subject to any disclaimer, the term of this patent is extended or adjusted under 35 U.S.C. 154(b) by 926 days.

(21) Appl. No.: 17/279,554

(22) PCT Filed: Sep. 10, 2019

(86) PCT No.: PCT/CN2019/105010
§ 371 (c)(1),
(2) Date: Mar. 24, 2021

(87) PCT Pub. No.: WO2020/063320
PCT Pub. Date: Apr. 2, 2020

(65) Prior Publication Data
US 2021/0393609 A1   Dec. 23, 2021

(30) Foreign Application Priority Data
Sep. 25, 2018  (CN) .......................... 201811112830.8

(51) Int. Cl.
| | | |
|---|---|---|
| A61K 31/46 | (2006.01) | |
| A61K 9/00 | (2006.01) | |
| A61K 47/02 | (2006.01) | |
| A61K 47/18 | (2017.01) | |
| A61K 47/36 | (2006.01) | |
| A61K 47/38 | (2006.01) | |
| A61K 47/54 | (2017.01) | |

(52) U.S. Cl.
CPC ............ *A61K 31/46* (2013.01); *A61K 9/0048* (2013.01); *A61K 47/02* (2013.01); *A61K 47/186* (2013.01); *A61K 47/36* (2013.01); *A61K 47/38* (2013.01); *A61K 47/547* (2017.08)

(58) Field of Classification Search
CPC ..... A61K 31/46; A61K 47/547; A61K 47/186
See application file for complete search history.

(56) References Cited

U.S. PATENT DOCUMENTS

| | | | |
|---|---|---|---|
| 9,421,199 B2 | 8/2016 | Ostrow et al. | |
| 2018/0325888 A1* | 11/2018 | Puri | ....................... A61K 47/38 |

FOREIGN PATENT DOCUMENTS

| | | | | |
|---|---|---|---|---|
| CN | 106572998 A | 4/2017 | | |
| CN | 107456440 A | 12/2017 | | |
| IN | 201611015904 A | 6/2016 | | |
| JP | H01203320 A | 8/1989 | | |
| JP | 2017522292 A | 8/2017 | | |
| JP | 2018021007 A | 2/2018 | | |
| SU | 417422 A1 | 7/1974 | | |
| WO | WO-2014102829 A1 * | 7/2014 | ........... | C07D 451/10 |
| WO | 2015/200361 A1 | 12/2015 | | |
| WO | WO-2016172712 A2 * | 10/2016 | ............. | A61K 31/46 |
| WO | WO-2018066651 A1 * | 4/2018 | ............. | A61K 47/02 |

OTHER PUBLICATIONS

WO2018066651 A1 Machine Translation (Year: 2018).*
English Translation of Chinese International Search Report mailed Dec. 13, 2019, for PCT/CN2019/105010, 3 pages.

* cited by examiner

*Primary Examiner* — Sarah Pihonak
*Assistant Examiner* — Mikhail O'Donnel Robinson
(74) *Attorney, Agent, or Firm* — Morgan, Lewis & Bockius LLP

(57) ABSTRACT

The application provides a method for improving the stability of a low-concentration atropine ophthalmic preparation, characterized by controlling the content of the total impurity ≤0.25% and/or a single impurity content of ≤0.05%, as well as a method for preparing the ophthalmic preparation, an atropine ophthalmic preparation prepared therefrom and use thereof in the manufacture of a medicament for preventing and/or treating vision defects.

25 Claims, 1 Drawing Sheet

METHOD FOR IMPROVING STABILITY OF LOW-CONCENTRATION ATROPINE OPHTHALMIC PREPARATION

CROSS-REFERENCES TO RELATED APPLICATIONS

This application is a U.S. national phase application of a PCT Application No. PCT/CN2019/105010 filed on Sep. 10, 2019, which claims priority to a Chinese Patent Application No. 201811112830.8 filed in China on Sep. 25, 2018, the disclosure of which is incorporated herein by reference in its entirety.

TECHNICAL FIELD

The application belongs to the field of pharmaceutical preparations, and specifically relates to a method for improving the stability of a low-concentration atropine ophthalmic preparation, as well as a method for preparing the ophthalmic preparation, and the atropine ophthalmic preparation prepared therefrom and uses thereof.

BACKGROUND ART

Atropine ophthalmic preparations have been used in clinic for many years, and mainly for mydriasis, cycloplegia and suppressive therapy in the treatment of amblyopia. In addition, atropine is currently the only medicament that has been proven by evidence-based medicine to effectively slow the progression of myopia, and its use to control the progression of myopia has a history of many years.

At present, there are not many drugs that can be used to control the progression of myopia in adolescents at home and abroad, and their side effects are not ignored. In China, atropine was mostly applied in high-concentration short-term therapy for the treatment of myopia in the past, and it was used to relieve convulsions, and the effect was not easy to consolidate after stopping the drug. At present, the specification of atropine ophthalmic preparations marketed in China is 1%. Due to the high concentration of atropine, there are side effects such as dilated pupils and blurred vision, which will affect the life and learning of patients to a certain extent, and cannot be used as a clinical routine drug for long-term medication to control the progression of myopia.

The use of low-concentration atropine ophthalmic preparations to prevent and treat myopia in adolescents has made some phased progresses. For example, the National Eye Center of Singapore Institute of Ophthalmology has carried out research on low-concentration atropine treatment for myopia for many years, and the results prove that, compared with other high-concentration atropine treatment groups, the low-concentration atropine treatment group had the least number of remaining myopia children, and had significantly reduced pupil dilation effect thereby greatly reducing the side effects of pupil dilation, blurred vision, photophobia, conjunctivitis and dermatitis caused by high-concentration atropine. Therefore, low-concentration atropine ophthalmic preparations are more suitable for adolescents to drip in eyes for long term to control the progression of myopia, and the rebound effect after withdrawal is significantly reduced.

However, as a muscarinic receptor antagonist, atropine has significantly lower stability in its low-concentration preparations (e.g., 0.001% to 0.05%) than in its high-concentration preparations (e.g., 0.1% to 1%), this makes it more challenging to obtain low-concentration atropine preparations with high stability.

Usually, formulation adjustment is the most effective way to improve the stability of the formulation. The stability of atropine ophthalmic preparation can be significantly improved by adjusting buffer system or lowering pH value. The inventors of the present invention found that for low-concentration atropine ophthalmic preparations, lower pH values are required to meet the requirements of stability, but the irritation increases significantly, not only affecting the compliance of patients, but also resulting in tear secretion and thus affecting the bioavailability of atropine. In the U.S. Pat. No. 9,421,199B2, deuterated water is used to improve the stability of low-concentration atropine eye drops, but the introduction of isotopes will inevitably affect the safety of product, and has higher requirements for production and quality control, limiting the development and promotion of the product. In summary, there is still a need for a low-concentration atropine preparation with high stability in the art.

CONTENTS OF THE INVENTION

The requirements for the active pharmaceutical ingredient of atropine sulfate are strict, and many countries make strict regulations in pharmacopoeias for the quality standards, especially the content of related substances, as shown in the following table:

| ChP2015 | EP8.0 | JPXVII | USP40 |
|---|---|---|---|
| Total impurities shall not exceed 1.0%. | Impurities E, H: ≤0.3%; Impurities A, B, C, D, F, G: ≤0.2%; Single unknown impurity: ≤0.1%; Total impurities: ≤0.5%. | Identification test | Impurity A: ≤0.3%; Other known: ≤0.2%; Single unknown: ≤0.1%; Total impurities: ≤0.5% |

The inventors of the present invention unexpectedly discovered that by further controlling the contents of the total impurities and/or single impurity of commercially available active pharmaceutical ingredient of atropine that already meets the above standards, the shelf-life stability of low-concentration atropine ophthalmic preparations can be significantly improved.

Therefore, in one aspect, the present application provides a method for improving the stability of an atropine sulfate preparation, characterized by controlling the content of the total impurity ≤0.25% (for example, ≤0.2%, ≤0.15%, ≤0.1%, ≤0.05%, or not detectable) and/or a single impurity ≤0.05% (for example, ≤0.01%, or not detectable), of the active pharmaceutical ingredient atropine sulfate. In some preferred embodiments, the single impurity is impurity A. In some preferred embodiments, the single impurity is impurity B. In some preferred embodiments, the single impurity is impurity C. In some preferred embodiments, the single impurity is impurity J. In some preferred embodiments, the single impurity is impurity K.

The impurity content of the active pharmaceutical ingredient atropine sulfate may be analyzed by HPLC. In some embodiments, the conditions of the HPLC are as follows: detection wavelength: 210 nm; chromatographic column: using octadecylsilane-bonded silica gel as filler (3 μm, 250 mm×4.6 mm); using a mixed solution (containing 1.7 g of sodium lauryl sulfate) of 606 ml of 3.5 g/L potassium dihydrogen phosphate solution (adjusted with phosphoric acid to pH 3.3) and 320 ml of acetonitrile as mobile phase A, and acetonitrile as mobile phase B; and performing gradient elution according to the following table:

| Time | Mobile phase A | Mobile phase B |
|------|----------------|----------------|
| 0    | 85             | 15             |
| 10   | 85             | 15             |
| 30   | 65             | 35             |

The concentration of the test sample solution is 1 mg/ml.

In some preferred embodiments, the preparation is an ophthalmic liquid preparation (for example, eye drops). In some preferred embodiments, the preparation has an atropine sulfate concentration of 0.001% to 0.1% (preferably 0.005% to 0.05%).

In another aspect, the present application provides a method for refining atropine sulfate, comprising the following steps:
slurry washing the active pharmaceutical ingredient atropine sulfate with a slurry washing solvent a, a slurry washing solvent b and a slurry washing solvent c, respectively; wherein
the slurry washing solvent a is a low polarity solvent;
the slurry washing solvent b is an acetone-water mixed solvent (the volume of water accounts for 2% to 10%, for example, 5%);
the slurry washing solvent c is a low-polarity solvent.

In some preferred embodiments, the slurry washing solvent a is acetone, ethanol-acetone mixed solvent, diethyl ether, ethanol-diethyl ether mixed solvent, methyl tert-butyl ether, isopropyl ether, petroleum ether (e.g., petroleum ether (60-90), petroleum ether (90-120)) or any combination thereof. In some preferred embodiments, the slurry washing solvent a is used in an amount of that, for per gram of atropine sulfate, 3 to 30 ml (for example, 5, 10, 15 or 20 ml) of the slurry washing solvent a is added. In some preferred embodiments, the slurry washing with slurry washing solvent a is performed at 0° C. to 50° C. (for example, room temperature or 40° C.). In some preferred embodiments, the slurry washing with slurry washing solvent a is performed for 0.5 to 6 hours (for example, 3 hours).

In some preferred embodiments, the slurry washing b is used in an amount of that, for per gram of atropine sulfate, 5 to 20 ml (for example, 10 or 15 ml) of the slurry washing solvent b is added. In some preferred embodiments, the slurry washing with slurry washing solvent b is performed at 0° C. to 50° C. (for example, room temperature or 40° C.). In some preferred embodiments, the slurry washing with slurry washing solvent b is performed for 0.5 to 6 hours (for example, 4 hours).

In some preferred embodiments, the slurry washing solvent c is ethanol-acetone mixed solvent, ethanol-diethyl ether mixed solvent, acetone, or any combination thereof. In some preferred embodiments, the slurry washing solvent c is used in an amount of that, for per gram of atropine sulfate, 3 to 30 ml (for example, 5 or 10 ml) of the slurry washing solvent c is added. In some preferred embodiments, the slurry washing with slurry washing solvent c is performed at 0° C. to room temperature (for example, 10° C.). In some preferred embodiments, the slurry washing with slurry washing solvent c is performed for 0.5 to 6 hours (for example, 1.5 hours).

In some preferred embodiments, before the slurry washing, the method further comprises a step of pulverizing the active pharmaceutical ingredient atropine sulfate. In some preferred embodiments, the method further comprises a step of passing the pulverized active pharmaceutical ingredient atropine sulfate through a 30 to 100 mesh sieve.

In some preferred embodiments, after the slurry washing, the method further comprises a step of filtrating and/or drying. In some preferred embodiments, the filtration is selected from suction filtration, pressure filtration and spin filtration. In some preferred embodiments, the drying is drying under reduced pressure.

In another aspect, the present application provides an atropine sulfate, which is prepared by the above method; or of which the content of the total impurity is ≤0.25% (for example, ≤0.2%, ≤0.15%, ≤0.1%, ≤0.05%, or not detectable) and/or a single impurity is ≤0.05% (for example, ≤0.01%, or not detectable).

In another aspect, the present application provides a pharmaceutical composition, comprising the abovementioned atropine sulfate and a pharmaceutically acceptable excipient.

In some preferred embodiments, the pharmaceutical composition is an ophthalmic liquid preparation, such as eye drops. In some preferred embodiments, in the pharmaceutical composition, the concentration of the atropine sulfate ranges from 0.001% to 0.1% (preferably 0.005% to 0.05%).

In some preferred embodiments, the weight composition of the pharmaceutical composition is as follows:

| | |
|---|---|
| atropine sulfate | 0.001% to 0.1% (preferably 0.005% to 0.05%); |
| thickening agent | 0.1% to 10%; |
| complexing agent | 0.001% to 0.05%; |
| pH adjusting agent | in an amount of adjusting pH of the pharmaceutical composition to 3.5 to 6.5; |
| and, water | the balance; | optionally, it further comprises 0.001% to 0.05% of bacteriostatic agent;
optionally, it further comprises 0.1% to 2% of osmotic pressure regulator.

In some preferred embodiments, the thickening agent is selected from cellulose derivative, cross-linked polyvinyl alcohol-pyrrolidone, sodium hyaluronate, polyvinylpyrrolidone, polyvinyl alcohol, polyethylene glycol and any combination thereof. In some preferred embodiments, the cellulose derivative is selected from hydroxypropylmethylcellulose, methylcellulose, hydroxypropylcellulose, hydroxypropylmethylcellulose, sodium carboxymethylcellulose and any combination thereof. In some preferred embodiments, the thickening agent is hydroxypropylmethylcellulose. In some preferred embodiments, the thickening agent in the pharmaceutical composition has a weight content of 0.5% to 10%, such as 0.5% to 8%, 0.5% to 5%, 0.5% to 3%, or 1% to 3%.

In some preferred embodiments, the complexing agent is selected from edetic acid, disodium edetate and calcium sodium edetate, preferably disodium edetate. In some preferred embodiments, the complexing agent in the pharmaceutical composition has a weigh content of 0.005% to 0.05%, for example, 0.005% to 0.03%, 0.005% to 0.02%, 0.005% to 0.01%, or 0.008% to 0.01%.

In some preferred embodiments, the bacteriostatic agent is selected from benzalkonium chloride, benzalkonium bromide, cetrimonium bromide, phenoxyethanol, phenethyl alcohol, p-hydroxybenzoate ester bacteriostatic agents and any combination thereof. In some preferred embodiments, the bacteriostatic agent is one selected from benzalkonium chloride and ethyl p-hydroxybenzoate or any combination thereof. In some preferred embodiments, the bacteriostatic agent is benzalkonium chloride. In some preferred embodiments, the bacteriostatic agent in the pharmaceutical composition has a weight content of 0.005% to 0.03%, for example, 0.005% to 0.02%, 0.006% to 0.02%, 0.006% to 0.012%, or 0.008% to 0.01%.

In some preferred embodiments, the pH adjusting agent is one or more selected from carbonic acid buffer system, phosphate buffer system, citric acid buffer system, acetic acid buffer system, barbituric acid buffer system, tris(hydroxymethyl) aminomethane buffer system, boric acid, borax, sodium hydroxide, hydrochloric acid, citric acid and salts thereof. In some preferred embodiments, the pH adjusting agent is boric acid and phosphate buffer system (for example, sodium dihydrogen phosphate-disodium hydrogen phosphate buffer system, potassium dihydrogen phosphate-dipotassium hydrogen phosphate buffer system). In some preferred embodiments, the pH adjusting agent in the pharmaceutical composition has a content that makes the pharmaceutical composition to have a pH of 4.0 to 6.0, such as 4.5 to 5.5.

In some preferred embodiments, the osmotic pressure regulator is selected from sodium chloride, glycerin, propylene glycol, mannitol, and any combination thereof. In some preferred embodiments, the osmotic pressure regulator is propylene glycol. In some preferred embodiments, the osmotic pressure regulator in the pharmaceutical composition has a weight content of 0.1% to 1%, 0.1% to 0.5%, or 0.1% to 0.3%.

In some preferred embodiments, the pharmaceutical composition is selected from Formulations 1 to 4:

| Formulation 1: | |
| --- | --- |
| atropine sulfate | 0.005% to 0.02%; |
| hydroxypropylmethylcellulose | 1%; |
| disodium edetate | 0.01%; |
| benzalkonium chloride | 0.01%; |
| sodium dihydrogen phosphate monohydrate | 0.25%; |
| disodium hydrogen phosphate | 0.0025%; |
| and, water | the balance; |

| Formulation 2: | |
| --- | --- |
| atropine sulfate | 0.005% to 0.02%; |
| hydroxypropylmethylcellulose | 1%; |
| sodium hyaluronate | 2%; |
| disodium edetate | 0.01%; |
| benzalkonium chloride | 0.01%; |
| sodium dihydrogen phosphate monohydrate | 0.25%; |
| disodium hydrogen phosphate | 0.0025%; |
| and, water | the balance; |

| Formulation 3: | |
| --- | --- |
| atropine sulfate | 0.005% to 0.01%; |
| hydroxypropylmethylcellulose | 1%; |
| propylene glycol | 0.3%; |
| disodium edetate | 0.01%; |
| benzalkonium chloride | 0.01%; |
| boric acid | 1.8%; |
| and, water | the balance; |

| Formulation 4: | |
| --- | --- |
| atropine sulfate | 0.005% to 0.01%; |
| hydroxypropylmethylenecellulose | 1%; |
| disodium edetate | 0.01%; |
| boric acid | 1.8%; |
| and, water | the balance. |

In another aspect, the present application provides a method for preparing the above-mentioned pharmaceutical composition, comprising the following steps:

dispersing and swelling the thickening agent in 60° C. to 90° C. (for example, 70° C. to 90° C., 80° C. to 90° C.) water, and replenishing 20° C. to 30° C. (for example, 20° C. to 25° C.) water for dissolution to obtain liquid a;

dissolving the pH adjusting agent, complexing agent, bacteriostatic agent, and optional osmotic pressure adjuster separately in 60° C. to 80° C. (for example, 65° C. to 80° C., 65° C. to 75° C.) water, cooling to below 30° C. (for example, room temperature) and adding the atropine sulfate, liquid b is obtained after dissolution;

mixing the liquid a and the liquid b, adding the balance of water to obtain the pharmaceutical composition;

optionally, the method further comprises a step of filtering the obtained pharmaceutical composition, preferably filtering the obtained pharmaceutical composition with a 0.22 μm filter membrane.

In another aspect, the present application further provides use of the pharmaceutical composition in the manufacture of a medicament for preventing and/or treating a vision defect (such as myopia, especially myopia in children or adolescents).

SPECIFIC MODELS FOR CARRYING OUT THE INVENTION

The embodiments of the present invention will be described in detail below in conjunction with examples, but those skilled in the art will understand that the following examples are only used to illustrate the present invention and should not be regarded as limiting the scope of the present invention. If specific conditions are not indicated in the examples, it shall be carried out in accordance with conventional conditions or conditions recommended by the manufacturer. The reagents or instruments used without giving manufacturer are all conventional products that can be purchased commercially; the tests without giving detection methods in the examples are carried out by common methods in the art, or referring to the detection methods as prescribed in the "Pharmacopoeia of the People's Republic of China" (2015 Edition).

The code and structure of each of the impurities in active pharmaceutical ingredient atropine sulfate are as follows:

| Code | Impurity structure |
|---|---|
| Impurity A | (structure: phenyl-C(=CH2)-C(=O)-O-tropane with N-CH3) |
| Impurity B | (structure: HO-CH2-CH(phenyl)-C(=O)-O-nortropane with HN) |
| Impurity C | (structure: HO-CH2-CH(phenyl)-C(=O)-OH) |
| Impurity J | (structure: phenyl-C(=CH2)-C(=O)-OH) |
| Impurity K | (structure: phenyl-CH(OH)-C(=O)-O-nortropane with HN) |

Example 1: Refining of Atropine Sulfate Bulk Drug

Figure 1:
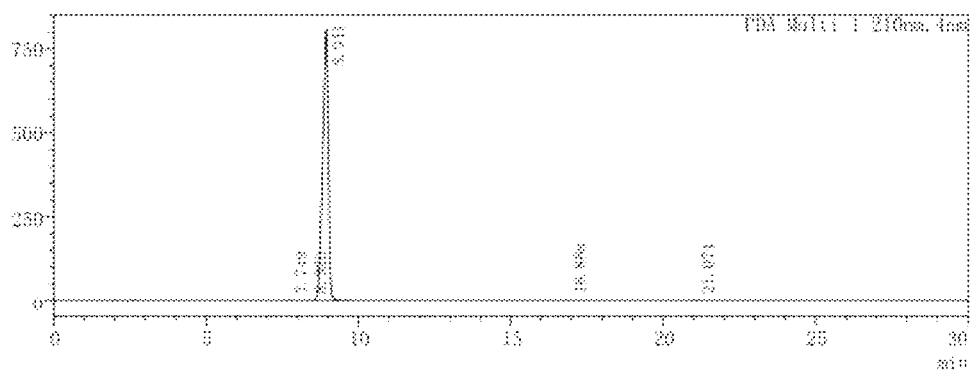
FIG. 1 shows the HPLC analysis spectrum of the commercially available active pharmaceutical ingredient atropine sulfate B160903.
Figure 2:
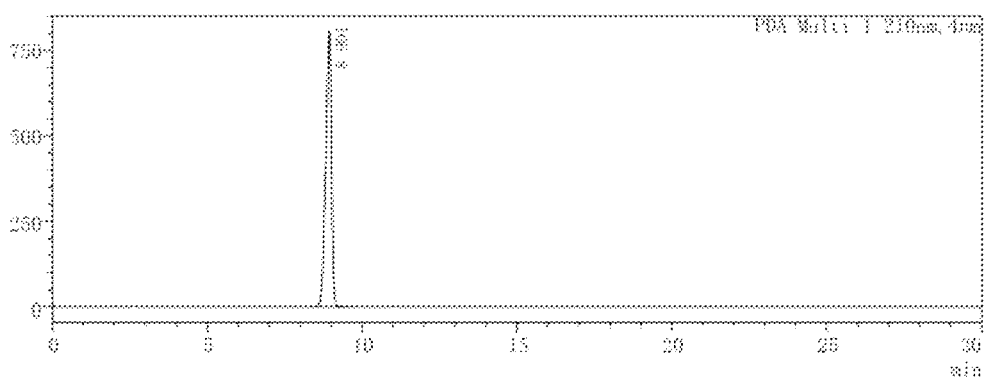
FIG. 2 shows the HPLC analysis spectrum of the 160903-P01 obtained after purification of the commercially available active pharmaceutical ingredient atropine sulfate B160903.

The commercially available active pharmaceutical ingredient atropine sulfate A or B with a purity of more than 99% was placed in a 60-mesh pulverizer, slowly pulverized and sieved, and the raw material under the sieve was collected for later use. 50 g of the pulverized active pharmaceutical ingredient was taken and placed in a 3000 mL three-necked flask, added with 20 times the amount of anhydrous acetone, stirred to perform slurry washing at 40° C. for 3 hours, and then subjected to suction filtration to obtain wet product 1. The wet product 1 was taken and placed in a 3000 mL three-necked flask, added with 15 times the amount of 5% acetone aqueous solution, stirred to perform slurry washing at 40° C. for 4 hours, and then subjected to suction filtration to obtain wet product 2. The wet product 2 was taken and placed in a 1000 mL three-necked flask, added with 10 times the amount of acetone, stirred to perform slurry washing at 5° C. for 1.5 hours, and then subjected to suction filtration, and dried under reduced pressure for 6 hours to obtain 41 g of atropine sulfate with a yield of 82%. The HPLC analysis of impurities was performed, and the results were shown in FIGS. 1 to 2 and Tables 1 to 2.

The HPLC analysis was carried out by a method as follows:

A sample of the above product was taken, dissolved and diluted by adding mobile phase A to obtain a solution with a concentration of 1 mg of product per 1 ml, as a sample solution; an appropriate amount of the sample solution was taken, dissolved and diluted by adding mobile phase A to obtain a solution with a concentration of 1 μg of atropine sulfate per 1 ml, as a control solution; another appropriate amount of atropine sulfate and impurity B were taken, dissolved and diluted by adding mobile phase to obtain a mixed solution with a concentration of about 1 μg/ml impurity B and about 1 mg/ml atropine sulfate per 1 ml, as a system suitability test solution. The analysis was carried out according to the high performance liquid chromatography (General Rules 0512, Chinese Pharmacopoeia, 2015 Edition), for which octadecylsilane-bonded silica gel was used as filler (3 μm, 250 mm×4.6 mm); [a mixed solution of 606 ml of 3.5 g/L potassium dihydrogen phosphate solution (adjusted to pH 3.3 with phosphoric acid) and 320 ml of acetonitrile] (containing 1.7 g of sodium lauryl sulfate) was used as mobile phase A, acetonitrile was used as mobile phase B, gradient elution was carried out according to the following table, and detection wavelength was 210 nm. 10 μl of the system suitability test solution was precisely taken and injected into the liquid chromatograph, and the degree of peak separation between atropine sulfate and impurity B should not be less than 2.0. 10 μl of the control solution and 10 μl of the sample solution were precisely taken and injected into the liquid chromatograph.

| Time | Mobile phase A | Mobile phase B |
|---|---|---|
| 0 | 85 | 15 |
| 10 | 85 | 15 |
| 30 | 65 | 35 |

If there were impurity peaks in the chromatogram of the sample solution, the impurity peaks, of which the relative retention time were before 0.25, should be subtracted, the peak areas of impurity A, impurity B, impurity C, impurity J and impurity K (see the table below for relative retention time and correction factors) should not be larger than the main peak area of the control solution (0.1%), the areas of other single impurity peaks should not be larger than the main peak area of the control solution (0.1%), and the sum of the areas of the impurity peaks should not be greater than 5 times (0.5%) of the main peak area of the control solution. In the chromatogram of the sample solution, the chromatographic peaks with peak area smaller than 0.5 times of the main peak area of the control solution should be ignored.

| Name of impurity | Structure of impurity | Relative retention time | Correction factor |
|---|---|---|---|
| Impurity A (dehydrated atropine) | (structure) | 2.17 | 0.47 |

-continued

| Name of impurity | Structure of impurity | Relative retention time | Correction factor |
|---|---|---|---|
| Impurity B (demethylatropine) | | 0.88 | 1 |
| Impurity C (tropic acid) | | 0.30 | 0.48 |
| Impurity J (atropic acid) | | 0.60 | 0.28 |
| Impurity K (homatropine) | | 0.82 | 0.84 |

TABLE 1

Purity comparison of commercially available active pharmaceutical ingredient atropine sulfate A before and after the refining

| | Active pharmaceutical ingredient A | | | Refined Active pharmaceutical ingredient A | | |
|---|---|---|---|---|---|---|
| | 150301 | 150601 | 160301 | 150301-P06 | 150601-P03 | 160301-P01 |
| Impurity A | 0.16% | 0.12% | 0.08% | Not detected | Not detected | Not detected |
| Impurity B | 0.09% | 0.07% | 0.11% | Not detected | Not detected | Not detected |
| Impurity C | Not detected | Not detected | Not detected | Not detected | Not detected | Not detected |
| Impurity J | Not detected | Not detected | Not detected | Not detected | Not detected | Not detected |
| Impurity K | Not detected | Not detected | Not detected | Not detected | Not detected | Not detected |
| Other single impurity | 0.13% | 0.07% | 0.19% | Not detected | Not detected | Not detected |
| Total impurities | 0.37% | 0.26% | 0.38% | Not detected | Not detected | Not detected |

TABLE 2

Purity comparison of commercially available active pharmaceutical ingredient atropine sulfate B before and after the refining

| | Active pharmaceutical ingredient B | | Refined Active pharmaceutical ingredient B | |
|---|---|---|---|---|
| Impurity | 160902 | 160903 | 160902-P01 | 160903-P01 |
| Impurity A | 0.16% | 0.13% | Not detected | Not detected |
| Impurity B | 0.01% | 0.01% | Not detected | Not detected |

TABLE 2-continued

Purity comparison of commercially available active pharmaceutical ingredient atropine sulfate B before and after the refining

| Impurity | Active pharmaceutical ingredient B | | Refined Active pharmaceutical ingredient B | |
|---|---|---|---|---|
| | 160902 | 160903 | 160902-P01 | 160903-P01 |
| Impurity C | Not detected | Not detected | Not detected | Not detected |
| Impurity J | Not detected | Not detected | Not detected | Not detected |
| Impurity K | Not detected | 0.02% | Not detected | Not detected |
| Other single impurity | 0.18% | 0.07% | Not detected | Not detected |
| Total impurities | 0.35% | 0.23% | Not detected | Not detected |

Example 2 to Example 6

According to the corresponding Formulation/Recipe in Table 3, the atropine ophthalmic preparations were prepared by the following preparation method.

Preparation Method:

(1) 10 g of 80° C. to 90° C. water for injection was taken, hydroxypropylmethylcellulose or sodium hyaluronate in prescribed amount was added thereto and fully dispersed and swelled, water for injection with a temperature of below 30° C. was replenished to make up 20 g, stirred for dissolution to obtain a transparent solution for later use;

(2) 50 g of water for injection with a temperature of 65° C. to 75° C. was taken, added with sodium dihydrogen phosphate monohydrate, disodium hydrogen phosphate, disodium edetate and benzalkonium chloride in prescribed amounts in sequence for dissolution, cooled by standing to below 30° C., added with the atropine sulfate refined according to the method in Example 1 in prescribed amount, stirred and dissolved;

(3) the hydroxypropylmethylcellulose solution obtained in (1) and the solution obtained in (2) were mixed uniformly;

(4) to the mixed solution obtained in (3), water was replenished to reach a total amount of 100 g, stirred evenly, sterilized by filtration with 0.22 μm filter membrane, and bottled.

Example 7 to Example 9

According to the corresponding Formulation/Recipe in Table 4, the atropine ophthalmic preparations were prepared by the following preparation method.

Preparation Method:

(1) 10 g of 80° C. to 90° C. water for injection was taken, hydroxypropylmethylcellulose in prescribed amount was added thereto and fully dispersed and swelled, water for injection with a temperature of below 30° C. was replenished to make up 20 g, stirred for dissolution to obtain a transparent solution for later use;

(2) 50 g of water for injection with a temperature of 65° C. to 75° C. was taken, added with boric acid, disodium edetate and benzalkonium chloride in prescribed amounts in sequence for dissolution, cooled by standing to below 30° C., added with the atropine sulfate refined according to the method in Example 1 in prescribed amount, stirred and dissolved;

(3) the hydroxypropylmethylcellulose solution obtained in (1) and the solution obtained in (2) were mixed uniformly;

(4) to the mixed solution obtained in (3), water was replenished to reach a total amount of 100 g, stirred evenly, sterilized by filtration with 0.22 μm filter membrane, and bottled.

TABLE 3

Formulation/Recipe

| Component | Example 2 | Example 3 | Example 4 | Example 5 | Example 6 |
|---|---|---|---|---|---|
| Atropine sulfate | 0.005 g | 0.010 g | 0.050 g | 0.010 g | 0.020 g |
| Hydroxypropylmethyl cellulose | 1.000 g | 1.000 g | 1.000 g | 1.000 g | 1.000 g |
| Sodium hyaluronate | — | — | — | 2.0 g | 2.0 g |
| Sodium dihydrogen phosphate monohydrate | 0.250 g | 0.250 g | 0.250 g | 0.250 g | 0.250 g |
| Disodium hydrogen phosphat | 0.0025 g | 0.0025 g | 0.0025 g | 0.0025 g | 0.0025 g |
| Disodium edetate | 0.010 g | 0.010 g | 0.010 g | 0.010 g | 0.010 g |
| Benzalkonium chloride | 0.010 g | 0.010 g | 0.010 g | 0.010 g | 0.010 g |
| Water for injection | The balance | The balance | The balance | The balance | The balance |

TABLE 4

| Component | Formulation/Recipe | | |
|---|---|---|---|
| | Example 7 | Example 8 | Example 9 |
| Atropine sulfate | 0.005 g | 0.010 g | 0.050 g |
| Hydroxypropylmethylcellulose | 1.000 g | 1.000 g | 1.000 g |
| Propylene glycol | 0.300 g | — | 0.300 g |
| Boric acid | 1.800 g | 1.800 g | 1.800 g |
| Disodium Edetate | 0.010 g | 0.010 g | 0.010 g |
| Benzalkonium chloride | 0.010 g | — | 0.010 g |
| Water for injection | The balance | The balance | The balance |

Comparative Example 1 to Comparative Example 5

According to the corresponding Formulation/Recipe in Table 3, the atropine ophthalmic preparations were prepared by the following preparation method.

Preparation Method:
(1) 10 g of 80° C. to 90° C. water for injection was taken, hydroxypropylmethylcellulose or sodium hyaluronate in prescribed amount was added thereto and fully dispersed and swelled, water for injection with a temperature of below 30° C. was replenished to make up 20 g, stirred for dissolution to obtain a transparent solution for later use;
(2) 50 g of water for injection with a temperature of 65° C. to 75° C. was taken, added with sodium dihydrogen phosphate monohydrate, disodium hydrogen phosphate, disodium edetate and benzalkonium chloride in prescribed amounts in sequence for dissolution, cooled by standing to below 30° C., added with the active pharmaceutical ingredient atropine sulfate B160903 in prescribed amount, stirred and dissolved;
(3) the hydroxypropylmethylcellulose solution obtained in (1) and the solution obtained in (2) were mixed uniformly;
(4) water was replenished to reach a total amount of 100 g, stirred evenly, sterilized by filtration with 0.22 μm filter membrane, and bottled.

Comparative Example 6 to Comparative Example 8

According to the corresponding Formulation/Recipe in Table 4, the atropine ophthalmic preparations were prepared by the following preparation method.

Preparation Method:
(1) 10 g of 80° C. to 90° C. water for injection was taken, hydroxypropylmethylcellulose in prescribed amount was added thereto and fully dispersed and swelled, water for injection with a temperature of below 30° C. was replenished to make up 20 g, stirred for dissolution to obtain a transparent solution for later use;
(2) 50 g of water for injection with a temperature of 65° C. to 75° C. was taken, added with boric acid, disodium edetate and benzalkonium chloride in prescribed amounts in sequence for dissolution, cooled by standing to below 30° C., added with the active pharmaceutical ingredient atropine sulfate B160903 in prescribed amount, stirred and dissolved;
(3) the hydroxypropylmethylcellulose solution obtained in (1) and the solution obtained in (2) were mixed uniformly;
(4) to the mixed solution obtained in (3), water was replenished to reach a total amount of 100 g, stirred evenly, sterilized by filtration with 0.22 μm filter membrane, and bottled.

Experimental Example 1: Accelerated Stability Experiment of Refined Active Pharmaceutical Ingredient Atropine Sulfate The active pharmaceutical ingredient atropine sulfate (batch number: 160903-P01) refined in Example 1 was taken and packaged (plastic sealed with medicinal low-density polyethylene bag as inner layer, aluminum barrel as outer layer), and stored under the condition of 40°±C.±2° C., relative humidity of 75%±5%, and the product changes were observed in the $0^{th}$ month, $1^{st}$ month, $2^{nd}$ month, $3^{rd}$ month, and $6^{th}$ month, respectively. The results were shown in Table 5.

TABLE 5

Accelerated stability observation results of refined active pharmaceutical ingredient atropine sulfate

| Observation item | | Limit requirement | $0^{th}$ month | $1^{st}$ month | $2^{nd}$ month | $3^{rd}$ month | $6^{th}$ month |
|---|---|---|---|---|---|---|---|
| Properties | | Colorless crystal or white crystalline powder, odorless | Colorless crystal or white crystalline powder, odorless | Colorless crystal or white crystalline powder, odorless | Colorless crystal or white crystalline powder, odorless | Colorless crystal or white crystalline powder, odorless | Colorless crystal or white crystalline powder, odorless |
| Melting point | | not be lower than 189° C., melting and decomposing simultaneously | 194.2° C.-195.8° C. | 193.8° C.-196.2° C. | 193.6° C.-195.8° C. | 193.2° C.-194.2° C. | 189.8° C.-191.0° C. |
| Acidity | | 4.5 to 6.2 | 4.91 | 4.86 | 4.86 | 4.58 | 5.24 |
| Hyoscyamine | | −0.40° to +0.05° | +0.002° | +0.002° | +0.001° | 0.000° | 0.000° |
| Related substances | Single impurity | Impurity A ≤ 0.1% | Not detected | Not detected | Not detected | Not detected | Not detected |
| | | Impurity B ≤ 0.1% | Not detected | Not detected | Not detected | Not detected | Not detected |
| | | Impurity C ≤ 0.1% | Not detected | Not detected | Not detected | Not detected | Not detected |
| | | Impurity J ≤ 0.1% | Not detected | Not detected | Not detected | Not detected | Not detected |
| | | Impurity K ≤ 0.1% | Not detected | Not detected | Not detected | Not detected | Not detected |
| | Total impurities | ≤0.5% | Not detected | Not detected | Not detected | Not detected | Not detected |
| Isomers | | Not more than 0.1% | Not detected | Not detected | Not detected | Not detected | Not detected |
| Moisture | | 2.0% to 4.0% | 3.15% | 3.24% | 2.97% | 3.49% | 3.69% |
| Content | | Not less than 99.0% | 100.3% | 100.3% | 100.2% | 100.4% | 100.3% |

Experimental Example 1: Comparative Experiment of Stability of Low-Concentration Atropine Ophthalmic Preparations The atropine ophthalmic preparations obtained in Examples 2 to 9 and Comparative Examples 1 to 8 were taken, stored under the condition of 40° C.±2° C., relative humidity of 25%±5%, and the content of active ingredient and the content of the main degradation product impurity C were tested in the $0^{th}$ month, $1^{st}$ month, $2^{nd}$ month, $3^{rd}$ month, and $6^{th}$ month, respectively. The results were shown in Table 6.

The method for determining the content of active ingredient was as follows: about 0.5 g of the ophthalmic preparation was taken, precisely weighed, added with 40 ml of acetic anhydride for dissolution, followed by addition of 1 to 2 drops of crystal violet indicator solution, titrated with perchloric acid titrant (0.1 mol/L) until the solution appeared pure blue, and the titration result was corrected with blank test. Each 1 ml of perchloric acid titrant (0.1 mol/L) was equivalent to 67.68 mg of $(C_{17}H_{23}NO_3)_2 \cdot H_2SO_4$.

The content of impurity C was determined by referring to the HPLC method in Example 1.

TABLE 6

Stability data of low-concentration atropine ophthalmic preparations

| Time | $0^{th}$ month Content (%) | $0^{th}$ month Impurity C (%) | $1^{st}$ month Content (%) | $1^{st}$ month Impurity C (%) | $2^{nd}$ month Content (%) | $2^{nd}$ month Impurity C (%) | $3^{rd}$ month Content (%) | $3^{rd}$ month Impurity C (%) | $6^{th}$ month Content (%) | $6^{th}$ month Impurity C (%) |
|---|---|---|---|---|---|---|---|---|---|---|
| Example 2 | 99.6 | Not detected | 98.5 | 0.06 | 99.3 | 0.11 | 99.0 | 0.15 | 99.3 | 0.27 |
| Comparative Example 1 | 100.4 | 0.02 | 99.5 | 0.32 | 99.7 | 0.6 | 98.7 | 0.87 | 97.1 | 1.73 |
| Example 3 | 100.6 | Not detected | 99.5 | 0.05 | 99.6 | 0.09 | 99.4 | 0.16 | 99.3 | 0.30 |
| Comparative Example 2 | 99.7 | 0.02 | 99.9 | 0.33 | 100.2 | 0.65 | 98.8 | 0.91 | 97.3 | 1.66 |
| Example 4 | 100.7 | Not detected | 100.2 | 0.07 | 99.8 | 0.11 | 99.7 | 0.15 | 99.8 | 0.29 |
| Comparative Example 3 | 100.3 | 0.02 | 99.3 | 0.29 | 99.8 | 0.61 | 98.2 | 0.88 | 97.9 | 1.81 |
| Example 5 | 99.8 | Not detected | 99.6 | 0.06 | 99.2 | 0.09 | 100.1 | 0.17 | 99.1 | 0.31 |
| Comparative Example 4 | 99.6 | 0.02 | 100.2 | 0.31 | 99.3 | 0.64 | 98.6 | 0.85 | 97.3 | 1.76 |
| Example 6 | 99.3 | Not detected | 99.3 | 0.04 | 99.2 | 0.12 | 98.2 | 0.16 | 100.6 | 0.28 |
| Comparative Example 5 | 99.0 | 0.02 | 100.1 | 0.27 | 98.2 | 0.58 | 98.3 | 0.89 | 98.1 | 1.69 |
| Example 7 | 101.2 | Not detected | 100.9 | 0.06 | 100.2 | 0.11 | 99.8 | 0.17 | 100.3 | 0.33 |
| Comparative Example 6 | 100.7 | 0.03 | 100.2 | 0.32 | 99.7 | 0.59 | 99.2 | 0.91 | 98.3 | 1.77 |
| Example 8 | 99.6 | Not detected | 99.7 | 0.08 | 99.9 | 0.09 | 100.1 | 0.18 | 99.1 | 0.29 |
| Comparative Example 7 | 100.8 | 0.03 | 99.2 | 0.35 | 98.7 | 0.71 | 99.1 | 0.92 | 97.3 | 1.81 |
| Example 9 | 101.9 | Not detected | 101.2 | 0.06 | 100.9 | 0.12 | 100.3 | 0.18 | 100.1 | 0.31 |
| Comparative Example 8 | 100.1 | 0.03 | 99.8 | 0.26 | 99.2 | 0.61 | 98.8 | 0.86 | 98.1 | 1.79 |

It can be seen from the data in Table 6 that as compared with products prepared by conventional processes, the low-concentration ophthalmic preparations prepared by using the atropine sulfate of the present application showed a significantly slower degradation rate of active ingredient and a significantly reduced content of the main degradation product impurity C, the stability of the low-concentration atropine sulfate ophthalmic preparations were significantly improved, the quality of product was improved, and the shelf-life of product was effectively extended.

Although the specific implementation of the present invention has been described in detail, according to all the teachings that have been disclosed, those skilled in the art can make various modifications and substitutions to the details of the technical solution of the present invention, and these changes are all within the protection scope of the present invention. The full scope of the invention is given by the appended claims and any equivalents thereof.

What is claimed is:

1. An atropine sulfate, wherein the content of the total impurity is ≤0.15% by weight and the content of a single impurity is ≤0.05% by weight upon formulation and remains upon storage at about 40° C. and about 75% relative humidity for at least about 6 months; wherein the single impurity comprises: impurity A:

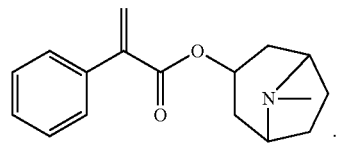 [SMILES: C=C(C(=O)OC1CC2CCC(C1)N2C)c1ccccc1]

2. A method for preparing the atropine sulfate according to claim 1, consisting of the following steps:
providing an active pharmaceutical ingredient atropine sulfate with a purity of more than 99% as a raw material;
optionally, pulverizing the active pharmaceutical ingredient atropine sulfate; optionally, passing the pulverized active pharmaceutical ingredient atropine sulfate through a 30 to 100 mesh sieve;
slurry washing the active pharmaceutical ingredient atropine sulfate with a slurry washing solvent a, a slurry washing solvent b and a slurry washing solvent c, respectively, so as to obtain a refined atropine sulfate; wherein, the slurry washing solvent a is acetone;

the slurry washing solvent b is an acetone-water mixed solvent, wherein the volume of water accounts for 2% to 10%;

the slurry washing solvent c is acetone; and optionally, filtrating and/or drying; wherein the filtration is selected from suction filtration, pressure filtration and spin filtration; the drying is drying under reduced pressure.

3. An atropine sulfate preparation, wherein the atropine sulfate preparation comprises the atropine sulfate according to claim 1.

4. A pharmaceutical composition, comprising the atropine sulfate according to claim 1 and a pharmaceutically acceptable excipient.

5. The pharmaceutical composition according to claim 4, its weight composition is as follows:

| | |
|---|---|
| atropine sulfate | 0.001% to 0.1% (preferably 0.005% to 0.05%); |
| thickening agent | 0.1% to 10%; |
| complexing agent | 0.001% to 0.05%; |
| pH adjusting agent | in an amount of adjusting pH of the pharmaceutical composition to 3.5 to 6.5; |
| and, water | the balance; | optionally, it further comprises 0.001% to 0.05% of bacteriostatic agent;
optionally, it further comprises 0.1% to 2% of osmotic pressure regulator.

6. The pharmaceutical composition according to claim 5, which is characterized by any of the following features:

(1) the thickening agent is selected from cellulose derivative, cross-linked polyvinyl alcohol-pyrrolidone, sodium hyaluronate, polyvinylpyrrolidone, polyvinyl alcohol, polyethylene glycol and any combination thereof; wherein, the cellulose derivative is selected from hydroxypropylmethylcellulose, methylcellulose, hydroxypropylcellulose, hydroxypropylmethylcellulose, sodium carboxymethylcellulose and any combination thereof;

(2) the thickening agent in the pharmaceutical composition has a weight content of 0.5% to 10%;

(3) the complexing agent is selected from edetic acid, disodium edetate and calcium sodium edetate;

(4) the complexing agent in the pharmaceutical composition has a weight content of 0.005% to 0.05%;

(5) the bacteriostatic agent is selected from benzalkonium chloride, benzalkonium bromide, cetrimonium bromide, phenoxyethanol, phenethyl alcohol, p-hydroxybenzoate ester bacteriostatic agents and any combination thereof;

(6) the bacteriostatic agent in the pharmaceutical composition has a weight content of 0.005% to 0.03%;

(7) the pH adjusting agent is one or more selected from carbonic acid buffer system, phosphate buffer system, citric acid buffer system, acetic acid buffer system, barbituric acid buffer system, tris(hydroxymethyl) aminomethane buffer system, boric acid, borax, sodium hydroxide, hydrochloric acid, citric acid and salts thereof;

(9) the osmotic pressure regulator is selected from sodium chloride, glycerin, propylene glycol, mannitol, and any combination thereof;

(10) the osmotic pressure regulator in the pharmaceutical composition has a weight content of 0.1% to 1%.

7. The composition according to claim 5, which is selected from Formulations 1 to 4:

| Formulation 1: | |
|---|---|
| atropine sulfate | 0.005% to 0.02%; |
| hydroxypropylmethylcellulose | 1%; |
| disodium edetate | 0.01%; |
| benzalkonium chloride | 0.01%; |
| sodium dihydrogen phosphate monohydrate | 0.25%; |
| disodium hydrogen phosphate | 0.0025%; |
| and, water | the balance; |

| Formulation 2: | |
|---|---|
| atropine sulfate | 0.005% to 0.02%; |
| hydroxypropylmethylcellulose | 1%; |
| sodium hyaluronate | 2%; |
| disodium edetate | 0.01%; |
| benzalkonium chloride | 0.01%; |
| sodium dihydrogen phosphate monohydrate | 0.25%; |
| disodium hydrogen phosphate | 0.0025%; |
| and, water | the balance; |

| Formulation 3: | |
|---|---|
| atropine sulfate | 0.005% to 0.01%; |
| hydroxypropylmethylcellulose | 1%; |
| propylene glycol | 0.3%; |
| disodium edetate | 0.01%; |
| benzalkonium chloride | 0.01%; |
| boric acid | 1.8%; |
| and, water | the balance; |

| Formulation 4: | |
|---|---|
| atropine sulfate | 0.005% to 0.01%; |
| hydroxypropylmethylenecellulose | 1%; |
| disodium edetate | 0.01%; |
| boric acid | 1.8%; |
| and, water | the balance. |

8. A method for preparing the pharmaceutical composition according to claim 5, comprising the following steps:

dispersing and swelling the thickening agent in 60° C. to 90° C. water, and replenishing 20° C. to 30° C. water for dissolution to obtain liquid a;

dissolving the pH adjusting agent, complexing agent, bacteriostatic agent, and optional osmotic pressure adjuster separately in 60° C. to 80° C. water, cooling to below 30° C. and adding the atropine sulfate, liquid b is obtained after dissolution;

mixing the liquid a and the liquid b, adding the balance of water to obtain the pharmaceutical composition;

optionally, filtering the obtained pharmaceutical composition.

9. A method for preventing and/or treating a vision defect, comprising a step of administering the pharmaceutical composition according to claim 5 to a subject in need of such treatment.

10. The method according to claim 2, wherein the slurry washing solvent a is used in an amount of that, for per gram of atropine sulfate, 3 to 30 ml of the slurry washing solvent a is added.

11. The method according to claim 2, wherein the slurry washing with slurry washing solvent a is performed at 0° C. to 50° C. for 0.5 to 6 hours.

12. The method according to claim 2, wherein the slurry washing solvent b is used in an amount of that, for per gram of atropine sulfate, 5 to 20 ml of the slurry washing solvent b is added.

13. The method according to claim 2, wherein the slurry washing with slurry washing solvent b is performed at 0° C. to 50° C. for 0.5 to 6 hours.

14. The method according to claim 2, wherein the slurry washing solvent c is used in an amount of that, for per gram of atropine sulfate, 3 to 30 ml of the slurry washing solvent c is added.

15. The method according to claim 2, wherein the slurry washing with slurry washing solvent c is performed at 0° C. to room temperature for 0.5 to 6 hours.

16. The pharmaceutical composition according to claim 4, which is an ophthalmic liquid preparation.

17. The pharmaceutical composition according to claim 16, wherein the concentration of the atropine sulfate ranges from 0.001% to 0.1%.

18. The method according to claim 9, wherein the vision defect is myopia.

19. The atropine sulfate according to claim 1, wherein the content of the total impurity is ≤0.1% upon formulation and remains upon storage at about 40° C. and about 75% relative humidity for at least about 6 months.

20. The atropine sulfate according to claim 1, wherein the content of the total impurity is ≤0.05% upon formulation and remains upon storage at about 40° C. and about 75% relative humidity for at least about 6 months.

21. The atropine sulfate according to claim 1, wherein the content of the total impurity is not detectable upon formulation and remains undetectable upon storage at about 40° C. and about 75% relative humidity for at least about 6 months.

22. The atropine sulfate according to claim 1, wherein the content of a single impurity is ≤0.01% upon formulation and remains upon storage at about 40° C. and about 75% relative humidity for at least about 6 months.

23. The atropine sulfate according to claim 1, wherein the content of a single impurity is not detectable upon formulation and remains undetectable upon storage at about 40° C. and about 75% relative humidity for at least about 6 months.

24. The atropine sulfate according to claim 1, wherein said single impurity further comprises one or more of the following:

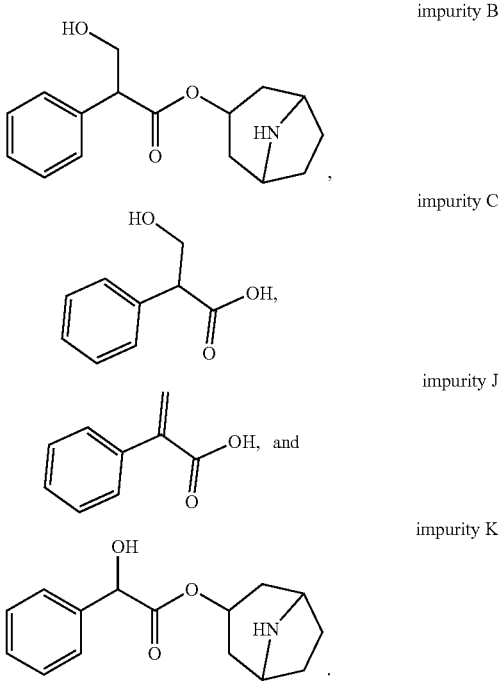

25. The method according to claim 2, wherein the slurry washing solvent b is an acetone-water mixed solvent, wherein the volume of water accounts for 2% to 5%.

* * * * *